United States Patent [19]
Abe

[11] Patent Number: 5,782,227
[45] Date of Patent: Jul. 21, 1998

[54] APPARATUS FOR CONTROLLING A HEATER FOR HEATING AN AIR-FUEL RATIO SENSOR

[75] Inventor: Shinichi Abe, Aichi, Japan

[73] Assignee: Toyota Jidosha Kabushiki Kaisha, Aichi, Japan

[21] Appl. No.: 877,688

[22] Filed: Jun. 17, 1997

[30] Foreign Application Priority Data

Jun. 25, 1996 [JP] Japan ................................. 8-164568

[51] Int. Cl.$^6$ ...................... G01N 27/416; F02D 41/14
[52] U.S. Cl. ...................... 123/689; 123/697; 204/425; 219/497
[58] Field of Search ...................... 123/686, 688, 123/689, 697; 73/23.32; 204/406, 408, 425; 219/497

[56] References Cited

U.S. PATENT DOCUMENTS 5,656,190  8/1997  Aoki ........................ 219/497 X

FOREIGN PATENT DOCUMENTS 60-214251  10/1985  Japan.
1-147138   6/1989   Japan.
1-158335   6/1989   Japan.
1-265148   10/1989  Japan.

Primary Examiner—Tony M. Argenbright
Attorney, Agent, or Firm—Kenyon & Kenyon

[57] ABSTRACT

An apparatus, for controlling a heater for heating an air-fuel ratio sensor, which is capable of preventing an excessive temperature rise of the heater after the air-fuel ratio sensor has been activated. After engine start-up, power is continuously supplied to the heater 112 until its temperature reaches about 1100° C. A basic power is determined so that the heater temperature is maintained at 1100° C. after reaching 1100° C., and so that the temperature of a sensing element 111 is maintained at 710° C. after the air-fuel ratio sensor has been activated. The basic power is corrected in increasing direction using an auxiliary power calculated as a function of coolant temperature. After the air-fuel ratio sensor has been activated, if the increased power exceeds the 1100° C. basic power, the power is limited below the 1100° C. base power, to prevent the heater being damaged due to an excessive temperature rise of the heater.

2 Claims, 6 Drawing Sheets

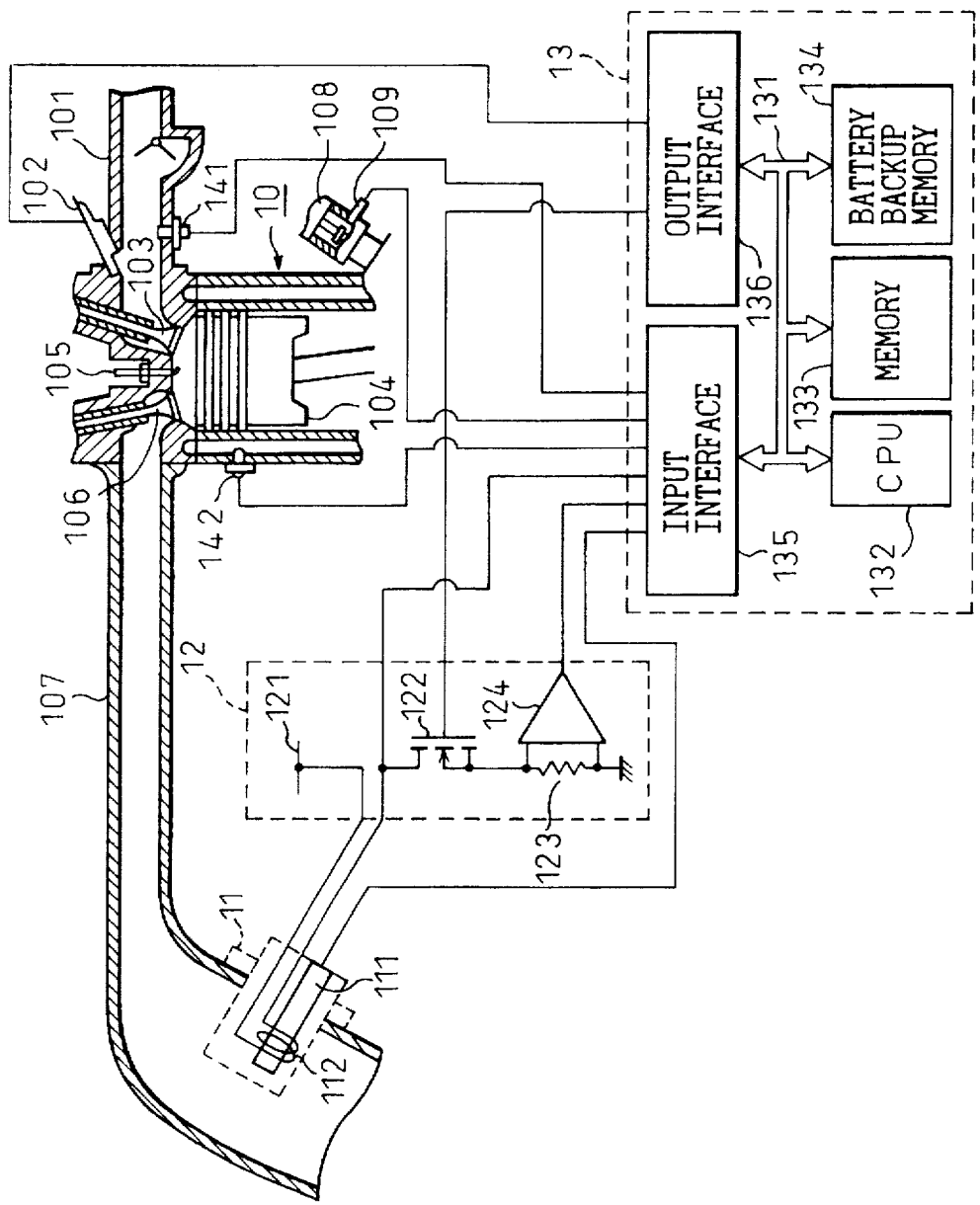

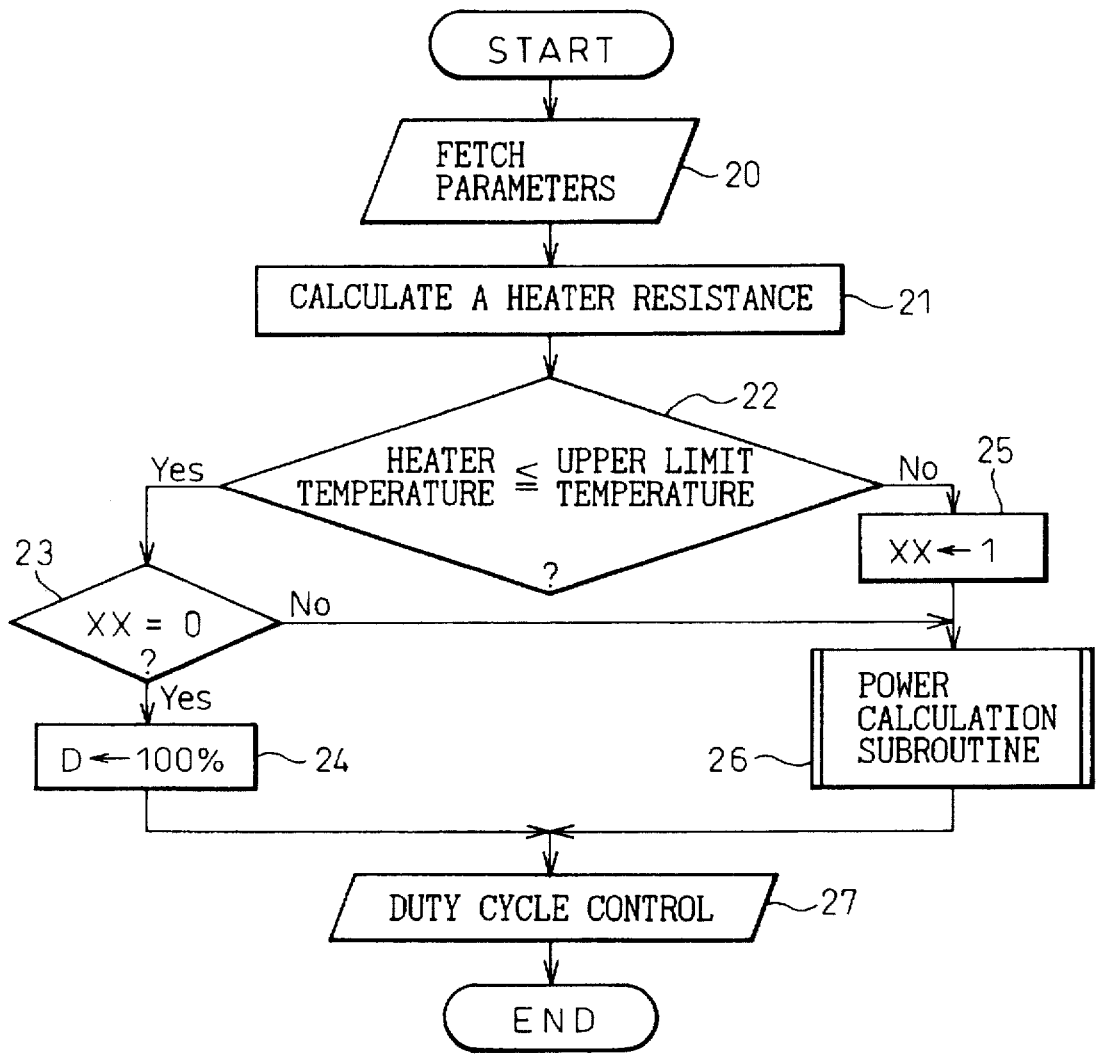

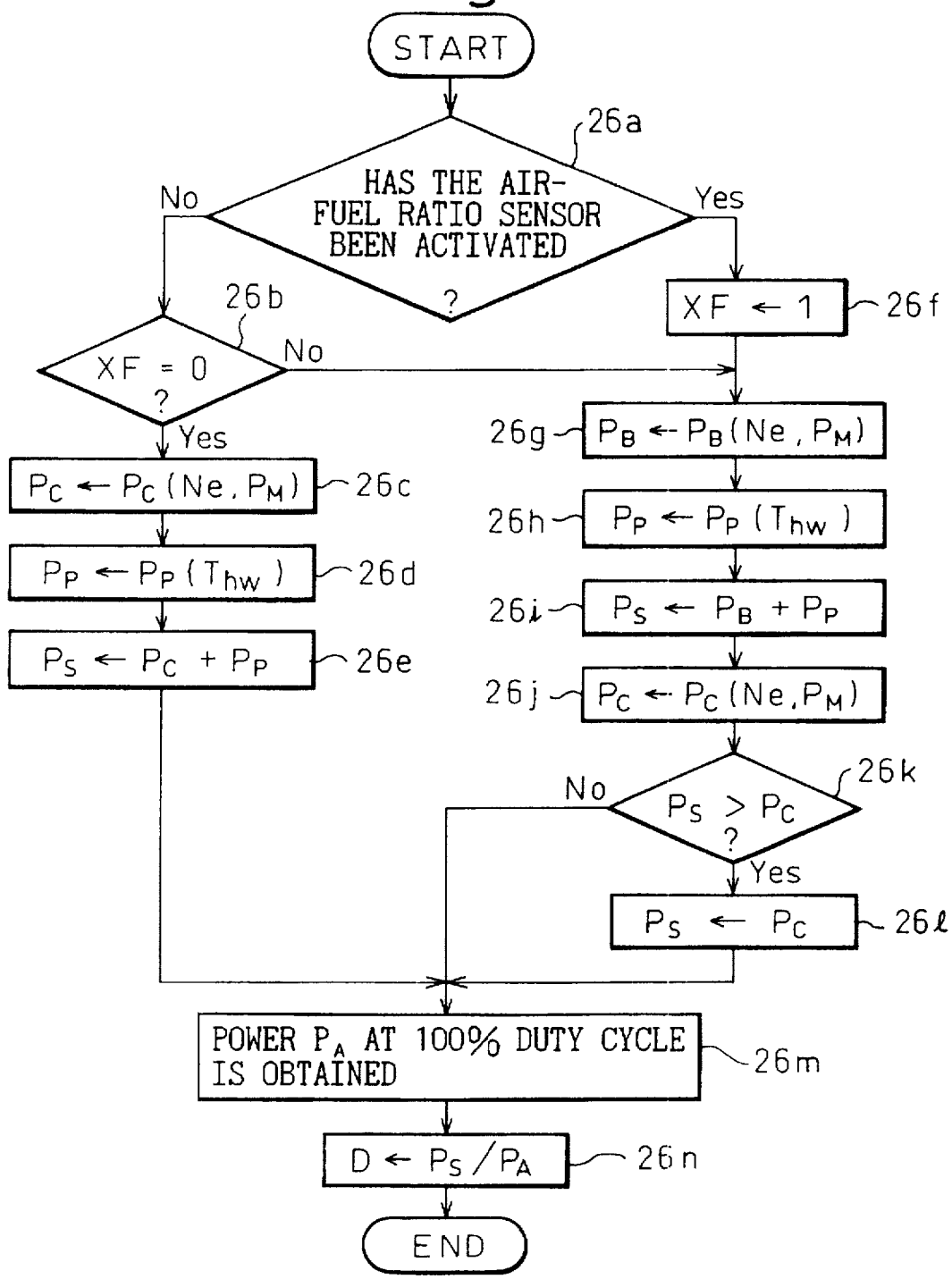

APPARATUS FOR CONTROLLING A HEATER FOR HEATING AN AIR-FUEL RATIO SENSOR

BACKGROUND OF THE INVENTION

1. Field of the Invention

The present invention relates to an apparatus for controlling a heater for heating an air-fuel ratio sensor, and more particularly to an apparatus, for controlling a heater for heating an air-fuel ratio sensor, which is capable of preventing an excessive temperature rise of the heater after activation of the air-fuel ratio sensor.

2. Prior Art

It is well known to control an air-fuel ratio of mixture supplied to a cylinder of an internal combustion engine at a target air-fuel ratio (for example, at the stoichiometric air-fuel ratio) by compensating for a basic injected amount of fuel in accordance with oxygen density of exhaust gas to improve automotive exhaust emission, specific fuel consumption and drivability.

For such an air-fuel ratio control, it is essential to detect the amount of oxygen contained in the exhaust gas. Since a sensor output voltage is affected not only by oxygen concentration but also by a temperature of the sensor itself, the sensor must be heated by a heater and be maintained at a fixed temperature of about 650° C. or above.

However, because the temperature is affected by the exhaust gas temperature, an apparatus for controlling the heater which controls a basic electric power supplied to the heater in accordance with the engine operating condition, and increases the basic electric power to accerelate the air-fuel ratio sensor before activating, has been proposed (See Unexamined Japanese Patent Application No. 1-158335).

By enlarging the above concept, it is also possible to supply the heater with a first basic power which is relatively large such that the heater is not deteriorated before the sensor is activated, and with a second basic power which is relatively small enough to maintain the activation of the sensor after the air-fuel ratio sensor has been activated.

The first basic power and the second basic power are both determined based on engine operating conditions after the engine has completely warmed up and when the exhaust gas temperature is high. Therefore, if the first basic power and the second basic power are supplied to the heater when the exhaust gas temperature is low, a sufficient heating power may not be obtained and there may occur a delay in the activation of the air-fuel ratio sensor.

It is possible to prevent the activation of the air-fuel sensor from being delayed by increasing the first basic power and the second basic power to solve the above problem, and it has already been proposed to determine an amount of increased power in accordance with a temperature of a coolant which correlates closely with the temperature of the exhaust gas (See Unexamined Japanese Patent Publication 1-147138).

It is unavoidable, however, that the power supplied to the heater after the air-fuel ratio sensor has been activated becomes larger than the first basic power which is not increased, when the second basic power is increased in accordance with the coolant temperature.

The first basic power is essentially determined as a relatively large power such that the heater is not deteriorated before the air-fuel ratio sensor is activated, but the heater is damaged due to the excess temperature rise of the heater when a power larger than the first basic power is supplied after the air-fuel ratio sensor has been activated.

SUMMARY OF THE INVENTION

In view of the above-outlined problems, it is an object of the present invention to provide an apparatus for controlling a heater for heating an air-fuel ratio sensor, which is capable of preventing an excessive temperature rise of the heater after the air-fuel ratio sensor has been activated.

According to the present invention, there is provided an apparatus for controlling a heater for heating an air-fuel ratio sensor installed in an exhaust pipe for detecting air-fuel ratio of exhaust gas, comprising: an operating condition detecting means for detecting an operating condition of an internal combustion engine; an activation determining means for determining that the air-fuel ratio sensor has been activated after the engine was started up; a basic electric power determining means for determining a first basic electric power in accordance with an operating condition of the engine detected by said operating condition detecting means when it is determined that the air-fuel ratio sensor has not been activated by said activation determining means, and for determining a second basic electric power less than the first electric power in accordance with an operating condition of the engine detected by said operating condition detecting means when it is determined that the air-fuel ratio sensor has been activated by said activation determining means; an auxiliary electric power determining means for determining an auxiliary electric power in accordance with a temperature of the coolant of the engine detected by said operating condition detecting means; a power increasing means for increasing the basic electric power determined by said basic electric power determining means in accordance with the auxiliary electric power determined by said auxiliary electric power determining means; and a heater controlling means for controlling an electric power supplied to the heater by limiting the electric power increased by said power increasing means to the first basic electric power by said basic electric power determining means.

According to this apparatus, a power supplied to the heater after the air-fuel ratio sensor has been activated is limited to below the first basic power.

BRIEF DESCRIPTION OF THE DRAWINGS

FIG. 1 is a diagram showing the configuration of an apparatus for controlling a heater for heating an air-fuel ratio sensor according to the present invention;

FIG. 2 is a flowchart of a heater control routine;

FIG. 3 is a flowchart of a power calculation subroutine;

DETAILED DESCRIPTION OF THE PREFERRED EMBODIMENTS

Figure 4A:
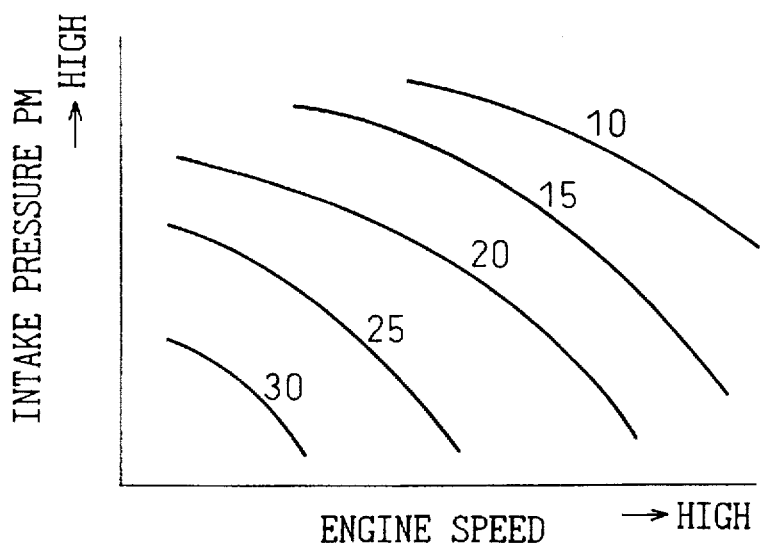
FIG. 4A and 4B are diagrams showing a basic power calculation maps.

FIG. 1 is a diagram showing the configuration of an apparatus for controlling a heater for heating an air-fuel ratio sensor according to the present invention. Air flowing through an intake manifold 101 and fuel injected from a fuel injector valve 102 are mixed together, and the air-fuel mixture is supplied through an intake valve 103 into an internal combustion engine 10.

The air-fuel mixture is compressed by a piston 104, and is ignited by a spark plug 105 when the piston 104 has reached near top dead center, producing power to push the piston 104 downward. After burning, the exhaust gas is discharged through an exhaust valve 106 into an exhaust manifold 107.

A speed of the internal combustion engine 10 is detected by an engine speed sensor 109 incorporated in a distributor 108.

A limiting-current type air-fuel ratio sensor 11 for detecting a residual oxygen concentration in the exhaust gas is mounted in the exhaust manifold 107. The air-fuel ratio sensor 11 consists of a sensing element 111 and a heater 112 for heating the sensing element 111.

The heater 112 is powered from a drive circuit 12 which consists of a power supply 121, a switching element 122, a current detection resistor 123, and a buffer amplifier 124.

More specifically, the heater 112, the switching element 122, and the current detection resistor 123 are connected in series between the power supply 121 and the ground (vehicle chassis). A current flowing through this series connection is detected by measuring the voltage developed across the current detection resistor 123 through the buffer amplifier 124.

There is also provided a controller 13 which is a microcomputer system comprising a CPU 132, a memory 133, a battery backup memory 134, an input interface 135, and an output interface 136, interconnected by a bus 131.

Data stored in the battery backup memory 134 will not be lost though the vehicle key is turned off (that is, though the ignition key is pulled out), unless the memory is removed from the battery (unless the memory is battery-cleared).

Not only the engine speed sensor 109 and the sensing element 111 of the air-fuel ratio sensor 11, but also an intake pressure sensor 141 mounted in the intake manifold 141 and a coolant temperature sensor 142 are connected to the input interface 134.

The output interface 135 outputs a valve opening command to the fuel injector valve 102 as well as on/off commands to the switching element 122.

FIG. 2 is a flowchart illustrating a heater control routine which is executed in the controller 13. This routine is executed every prescribed intervals.

At step 20, an engine speed $N_e$, an intake pressure $P_M$, a voltage $V_h$ at the downstream of the heater, a current $I_h$ flowing through the heater, and a coolant temperature $T_{hw}$ are fetched.

At step 21, a heater resistance $R_h$ is calculated from a battery voltage $V_B$, a heater downstream voltage $V_h$, and a heater current $I_h$, using the equation below.

$$R_h = (V_B - V_h)/I_h$$

At step 22, it is determined whether or not the heater temperature is less than or equal to a predetermined upper limit temperature (for example, 1100° C.), that is, whether or not the heater resistance $R_h$ is less than or equal to an upper limit resistance corresponding to the upper limit temperature.

When the determination at step 22 is affirmative, that is, when the heater temperature is not higher than the upper limit temperature, the control proceeds to step 23 to check whether or not flag XX, which indicates that the heater temperature has not exceeded the upper limit temperature after the engine was started, is "0", that is, whether or not the heater temperature has ever risen above the upper limit temperature since the engine was started. Note the flag XX was initialized to 0 by an initialization routine, not shown, when the engine was started.

When the determination at step 23 is affirmative, that is, when the heater temperature has never risen above the upper limit temperature since the engine was started, then the control proceeds to step 24, where duty cycle D is set to 100% to expedite activation of the air/fuel ratio sensor 11. The control then proceeds to step 27.

Conversely, when the determination at step 22 is negative, that is, when the heater temperature is above the upper limit temperature, the control proceeds to step 25, where the flag XX is set to 1, and then the control proceeds to step 26. Note, when the determination at step 23 is negative, that is, when the heater temperature has risen above the upper limit temperature since the engine was started, the control also proceeds to step 26.

At step 26, a power calculation subroutine is executed, and the control proceeds to step 27. At step 27, the switching element 122 is controlled in accordance with the duty cycle D determined at step 24 or step 26, and the routine is terminated.

FIG. 3 is a flowchart illustrating the power calculation subroutine executed at step 26. At step 26a, it is determined whether or not the air-fuel ratio sensor 11 has been activated. It can be determined, for example, by checking whether or not the output response curve of the air-fuel ratio sensor 11 has exceeded a fixed predetermined length.

When the determination at step 26 is negative, that is, when the air-fuel ratio sensor 11 has not yet been activated, then the control proceeds to step 26b to check whether or not a flag XF, which indicates whether or not the air-fuel ratio sensor 11 has been activated since the engine was started, is 0. When the flag XF is 0, the control proceeds to step 26c. Note, the flag XF was previously initialized to 0 by an initialization routine not shown.

In step 26c, based on a heater temperature 1100° C. map which is a function of the engine speed $N_e$ and intake pressure $P_M$, the basic power $P_C$ for 1100° C. which is required to maintain the heater temperature at 1100° C. is obtained.

$$P_C = P_C(N_e, P_M)$$

The 1100° C. map is used to determine the basic power $P_C$ for 1100° C. required to maintain the heater temperature at 1100° C. when the engine has completely warmed up and the exhaust gas temperature is sufficiently high. While the engine is warming-up, however, the exhaust gas is still low, and it is impossible to maintain the heater temperature at 1100° C. by applying only the 1100° C. basic power $P_C$. Accordingly, at step 26d, an auxiliary power $P_P$ is obtained as a function of the coolant temperature $T_{hw}$, and at step 26e, the auxiliary power $P_P$ is added to the 1100° C. basic power $P_C$ to obtain a supplied power $P_S$. After that, the control proceeds to step 26m.

$$P_P = P_P(T_{hw})$$

$$P_S = P_C + P_P$$

Conversely, when the determination at step 26a is affirmative, that is, when it is determined that the air-fuel ratio sensor 11 has been activated, the flag XF is set to 1 at step 26f, and the control proceeds to step 26g. Note, when the determination at step 26b is negative, that is, when the air-fuel ratio sensor 11 has been activated since the engine was started, the control always proceeds to step 26g.

At step 26g, based on an element temperature 710° C. map which is a function of the engine speed $N_e$ and the intake pressure $P_M$, a basic power $P_B$ for 710° C., which is required to maintain the heater temperature at 710° C. in order to maintain the sensing element 111 of the air-fuel sensor 11 at at least about 650° C., considering manufacturing error of the air-fuel ratio sensing element 111, is obtained.

$$P_B = P_B(N_e, P_M)$$

The 710° C. map is used to determine the base power $P_B$ for 710° C. required to maintain the temperature of the sensing element 111 of the air-fuel ratio sensor at 710° C. when the engine has completely warmed up and the exhaust gas temperature is sufficiently high. While the engine is warming-up, however, the exhaust gas temperature is still low, and it would not be possible to maintain the temperature of the sensing element 111 at 710° C. by applying only the 710° C. base power $P_B$. Accordingly, at step 26h, an auxiliary power $P_P$ is obtained as a function of the coolant temperature $T_{hw}$, and at step 26i, the auxiliary power $P_P$ is added to the 710° C. basic power $P_B$ to obtain a supplied power $P_S$.

$$P_P = P_P(T_{hw})$$

$$P_S = P_B + P_P$$

At step 26j, based on the 1100° C. map which is a function of the engine speed $N_e$ and intake pressure $P_M$, a basic power $P_C$ for 1100° C., which is required to maintain the heater temperature at 1100° C., is obtained.

$$P_C = P_C(N_e, P_M)$$

At step 26k, it is determined whether or not the supply power $P_S$ is larger than the 1100° C. basic power $P_C$. When the determination at 26k is affirmative, that is, when the supplied power Ps is larger than the 1100° C. basic power $P_C$, then it is determined that the supply power is excessive and may cause damage to the heater, and the control proceeds to step 26l, where the supplied power $P_S$ is limited to the 1100° C. base power $P_C$, before proceeding to step 26m.

Conversely, when the determination at step 26k is negative, that is, when the supplied power $P_S$ is less than the 1100° C. base power $P_C$, the control proceeds directly to step 26m.

The supplied power $P_A$ when the duty cycle is set to 100% is obtained at step 26m, the duty cycle D is calculated by the equation below at step 26n, and then this subroutine is terminated.

$$D = P_S/P_A$$

Figure 4B:
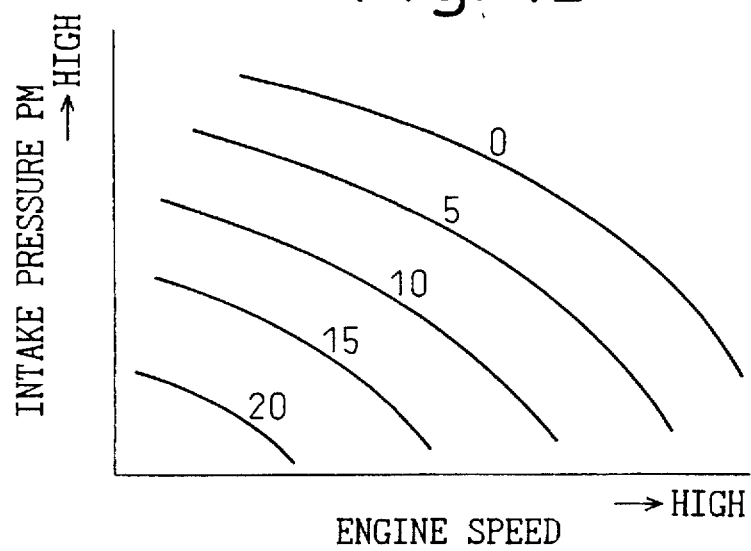

FIG. 4A and 4B show the basic power calculation maps, where the engine speed $N_e$ is plotted along the abscissa and the intake pressure $P_M$ along the ordinate. The parameter is the basic power.

Here, FIG. 4A shows the heater temperature 1100° C. map, and FIG. 4B shows the element temperature 710° C. map. For the same engine speed and intake pressure, the 1100° C. basic power $P_C$ is larger than the 710° C. basic power $P_B$.

Figure 5:
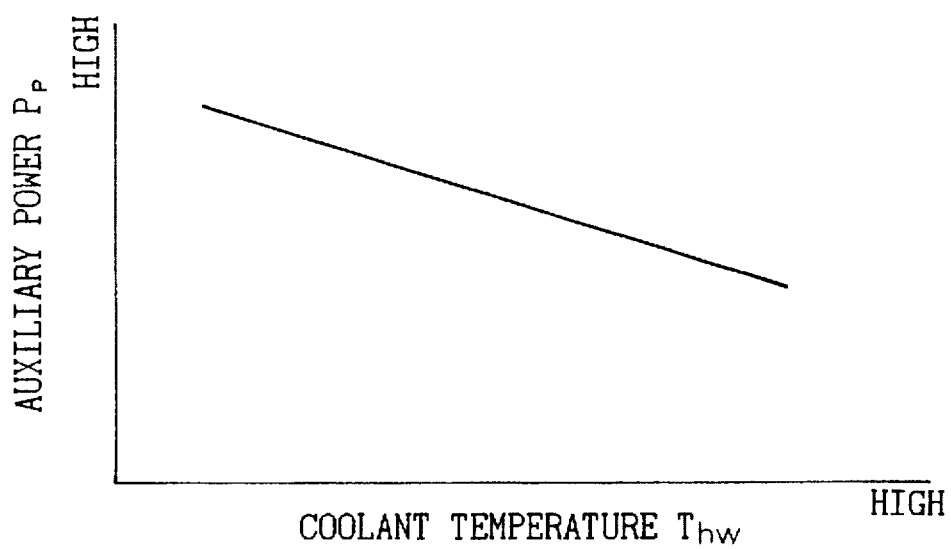
FIG. 5 is an auxiliary power calculation map.

FIG. 5 shows a map for calculating the auxiliary power P. and the auxiliary power $P_P$ is a function of the coolant temperature $T_{hw}$ such that the auxiliary power decreases as the coolant temperature rises.

Figure 6A:
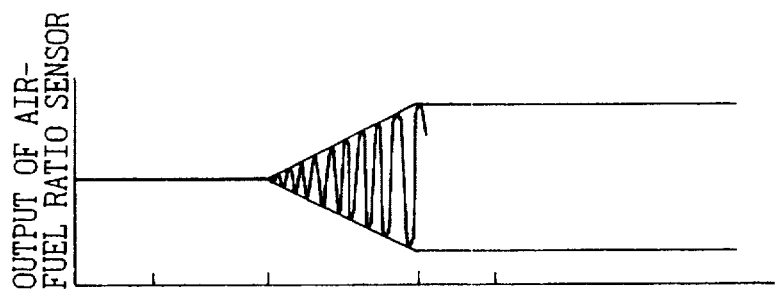
FIG. 6A–6C are diagrams for explaining the operation of the apparatus according to the present invention.
Figure 6B:
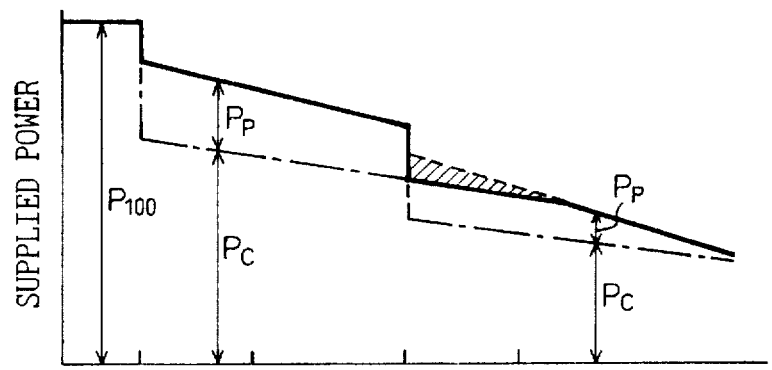
Figure 6C:
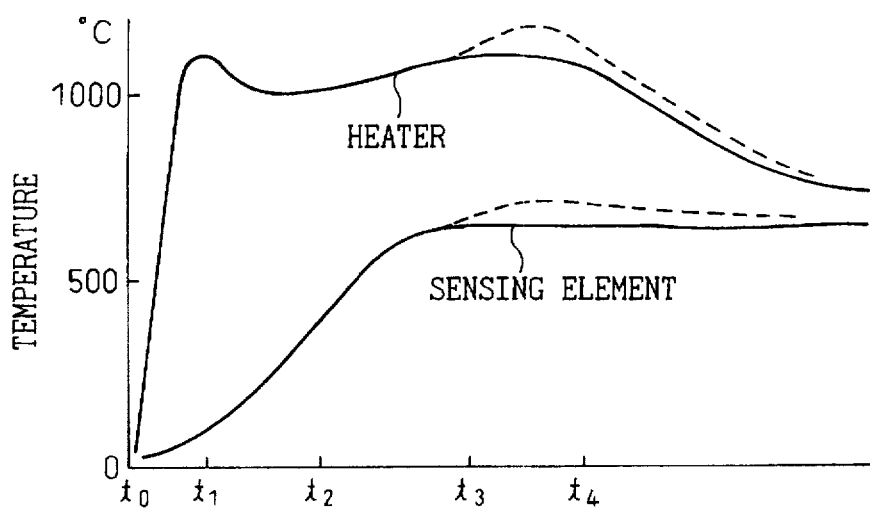

FIG. 6A-6C are diagrams for explaining the operation of the apparatus according to the present invention, and FIG. 6A shows the output of the air-fuel ratio sensor, FIG. 6B shows the supplied power, and FIG. 6C shows the air-fuel ratio sensor.

When the engine is started at time $t_0$, an electric power is continuously supplied to the heater 112 (by the 100% duty cycle control) so that the temperature of the heater 112 rapidly rises.

When the temperature of the heater 112 reaches about 1100° C. at time $t_1$, control of the power supplied to the heater is switched from the continuous energizing control to the duty control designed to regulate the supplied power at the sum of the 1100° C. basic power $P_C$ and the auxiliary power $P_P$, that is, the target power.

As the air-fuel ratio sensor 11 is heated, the output amplitude of the air-fuel ratio sensor 11 increases gradually after time $t_2$, and it is determined at time $t_3$ that the air-fuel ratio sensor 11 has been activated.

At time $t_3$, control for the power supplied to the heater is switched to the duty control designed to regulate the supplied power to the sum of the 710° C. base power $P_B$ and the correction power $P_P$. $(P_B+P_P)$.

If the target power of $(P_B+P_P)$ continues to be supplied after time $t_3$, $(P_B+P_P)$ may become greater than $P_C$ between time $t_3$ and time $t_4$, and may cause damage to the heater because the temperature rises above 1110° C. as shown by the dashed line in (C).

In the present invention, the target power supplied between time $t_3$ and time $t_4$ is limited by $P_C$, and the power is reduced as shown by the shaded portion in FIG. 6B, and the heater temperature is limited below 1100° C., as shown by the solid line in (C), to prevent the heater being damaged.

According to the apparatus of the present invention, after the engine is started, if the power supplied to the heater after the air-fuel ratio sensor has been activated, which is equal to the sum of the relatively small second basic power and the auxiliary power determined according to the coolant temperature, exceeds the relatively large first basic power before the air-fuel ratio sensor has been activated, the power supplied to the heater is limited to below the first base power. This prevents the heater being damaged by an excessive temperature rise of the heater.

I claim:

1. An apparatus for controlling a heater for heating an air-fuel ratio sensor installed in an exhaust pipe for detecting an air-fuel ratio of an exhaust gas, comprising:

an operating condition detecting means for detecting an operating condition of an internal combustion engine;

an activation determining means for determining that the air-fuel ratio sensor has been activated after the engine was started up;

a basic electric power determining means for determining a first basic electric power in accordance with an operating condition of the engine detected by said operating condition detecting means when it is determined that the air-fuel ratio sensor has not been activated by said activation determining means, and for determining a second basic electric power less than the first electric power in accordance with an operating condition of the engine detected by said operating condition detecting means when it is determined that the air-fuel ratio sensor has been activated by said activation determining means;

an auxiliary electric power determining means for determining an auxiliary electric power in accordance with a temperature of coolant of the engine detected by said operating condition detecting means;

a power increasing means for increasing the basic electric power determined by said basic electric power determining means in accordance with the auxiliary electric power determined by said auxiliary electric power determining means; and a heater controlling means for controlling an electric power supplied to the heater by limiting the electric power increased by said power increasing means to the first basic electric power by said basic electric power determining means.

2. A method for controlling a heater for heating an air-fuel ratio sensor installed in an exhaust pipe for detecting an air-fuel ratio of an exhaust gas, comprising the steps of:

an operating condition detecting step for detecting an operating condition of an internal combustion engine;

an activation determining step for determining that the air-fuel ratio sensor has been activated after the engine was started up;

a basic electric power determining step for determining a first basic electric power in accordance with an operating condition of the engine detected at said operating condition detecting step when it is determined that the air-fuel ratio sensor has not been activated at said activation determining step, and for determining a second basic electric power less than the first electric power in accordance with an operating condition of the engine detected at said operating condition detecting step when it is determined that the air-fuel ratio sensor has been activated by said activation determining step;

an auxiliary electric power determining step for determining an auxiliary electric power in accordance with a temperature of coolant of the engine detected at said operating condition detecting step;

a power increasing means for increasing the basic electric power determined at said basic electric power determining step in accordance with the auxiliary electric power determined at said auxiliary electric power determining step; and a heater controlling step for controlling an electric power supplied to the heater by limiting the electric power increased at said power increasing step to the first basic electric power determined at said basic electric power determining step.

* * * * *